(12) United States Patent
Agarwal et al.

(10) Patent No.: US 9,357,917 B2
(45) Date of Patent: Jun. 7, 2016

(54) METHOD AND APPARATUS FOR MANAGING BLINKING

(71) Applicant: Motorola Mobility LLC, Chicago, IL (US)

(72) Inventors: Nidhi Agarwal, Bangalore (IN); Amit Kumar Agrawal, Bangalore (IN)

(73) Assignee: Google Technology Holdings LLC, Mountain View, CA (US)

( * ) Notice: Subject to any disclaimer, the term of this patent is extended or adjusted under 35 U.S.C. 154(b) by 11 days.

(21) Appl. No.: 14/341,919

(22) Filed: Jul. 28, 2014

(65) Prior Publication Data

US 2016/0022135 A1    Jan. 28, 2016

(51) Int. Cl.
| | |
|---|---|
| A61B 3/00 | (2006.01) |
| A61B 3/113 | (2006.01) |
| A61B 3/14 | (2006.01) |
| G06K 9/00 | (2006.01) |

(52) U.S. Cl.
CPC . *A61B 3/113* (2013.01); *A61B 3/14* (2013.01); *G06K 9/00617* (2013.01)

(58) Field of Classification Search
CPC ................................ A61B 3/102; A61B 3/113
USPC ................. 351/223, 237, 239, 240, 222, 246; 348/62
See application file for complete search history.

(56) References Cited

U.S. PATENT DOCUMENTS

| | | | |
|---|---|---|---|
| 5,333,009 A | 7/1994 | Gell, Jr. et al. | |
| 5,384,593 A | 1/1995 | Gell, Jr. et al. | |
| 5,888,173 A | 3/1999 | Singhal | |
| 5,933,130 A | 8/1999 | Wagner | |
| 7,797,771 B1 | 9/2010 | Bossen et al. | |
| 8,195,475 B1 | 6/2012 | Landsman et al. | |
| 9,072,465 B2* | 7/2015 | Pugh ..................... | A61B 5/1103 |
| 2013/0110617 A1 | 5/2013 | Phan et al. | |
| 2014/0192325 A1* | 7/2014 | Klin ......................... | A61B 5/16 351/209 |

FOREIGN PATENT DOCUMENTS

| | | |
|---|---|---|
| WO | 201246823 A1 | 11/2012 |
| WO | 2013162510 A1 | 10/2013 |

OTHER PUBLICATIONS

Amanda Gardner, "Smartphones may be taxing your eyes", USA Today, Jul. 25, 2011, Retrieved from http://usatoday30.usatoday.com/news/health/story/health/story/2011/07/Smartphones-may-be-taxing-your-eyes/49649926/1, 2 pgs.

(Continued)

*Primary Examiner* — Hung Dang
(74) *Attorney, Agent, or Firm* — Shumaker & Sieffert, P.A.

(57) ABSTRACT

A method and apparatus for managing blinking includes an electronic computing device detecting blinking of a user of the electronic computing device and determining an uninduced blink rate for the user from the detected blinking. The method also includes inducing the user to blink based on the uninduced blink rate. A further method and apparatus for managing blinking includes the electronic computing device presenting the user with a blink inducement of a plurality of blink inducements and determining whether the user blinked in response to presenting the blink inducement. The further method also includes presenting the blink inducement again based on the determination of whether the user blinked in response to presenting the blink inducement.

20 Claims, 9 Drawing Sheets

(56) References Cited

OTHER PUBLICATIONS

WebMD, Eye Fatigue: Causes, Symptoms, and Treatment, Sep. 8, 2014, Retrieved from http://www.webmd.com/eye-health/eye-fatigue-causes-symptoms-treatment, 4 pgs.

The Vision Council, Hindsight is 20/20/20: Protect Your Eyes from Digital Devices, 2015 Digital Eye Strain Report, Jan. 7, 2015, Retrieved from https://www.thevisioncouncil.org/sites/default/files/VC_DigitalEyeStrain_Report2015.pdf, 15 pgs.

Adam Boettiger, "Five Tips for Preventing Eye Strain While Using Mobile Devices", Internet Archive WayBack Machine, Nov. 2011, Retrieved from https://web.archive.org/web/20111102203754/http://digitalminimalism.com/2011/fivetipsforpreventingeyestrainwhileusingmobiledevices/, 5 pgs.

\* cited by examiner

| INDUCEMENT | ATTEMPTS | SUCCESSES | SCORE |
|---|---|---|---|
| $I_1$ | 4 | 4 | 1.0 |
| $I_4$ | 4 | 4 | 1.0 |
| $I_3$ | 4 | 3 | .75 |
| $I_5$ | 4 | 3 | .75 |
| $I_6$ | 4 | 3 | .75 |
| $I_2$ | 4 | 2 | .5 |
| $I_7$ | 4 | 2 | .5 |
| $I_8$ | 4 | 1 | .25 |

| INDUCEMENT | ATTEMPTS | SUCCESSES | SCORE |
|---|---|---|---|
| $I_1$ | 10 | 9 | .9 |
| $I_3$ | 8 | 6 | .75 |
| $I_5$ | 6 | 4 | .667 |
| $I_4$ | 8 | 5 | .625 |
| $I_6$ | 7 | 4 | .571 |
| $I_7$ | 4 | 2 | .5 |
| $I_8$ | 7 | 3 | .429 |
| $I_2$ | 5 | 2 | .4 |

FIG. 6

METHOD AND APPARATUS FOR MANAGING BLINKING

FIELD OF THE DISCLOSURE

The present disclosure relates generally to managing blinking and more particularly to inducing a user of an electronic computing device to blink based on an uninduced blink rate for the user.

BACKGROUND

Since 1971, when the Intel Corporation introduced the world to the first microprocessor, the Intel 4004 (U.S. Pat. No. 3,821,715), society has become increasingly dependent upon electronic computing devices. Such devices are currently relied on for communication, data processing, business, and entertainment. It is not uncommon today for an office worker to spend many hours each day viewing a display screen of an electronic computing device. It is also not uncommon for today's youth to spend many hours at a time viewing a display screen while playing video games.

Comprehensive studies conducted by medical professionals show that long periods of time spent viewing display screens, especially at close distances, adversely affects eye health. The eyes are in a relaxed state when focused at a distance. With close-up viewing of a display screen, the muscles of the eyes must change the shape of the eyes to maintain focus. Further, individuals blink less often while focusing on display screens. Blinking is a natural process by which the eyes lubricate themselves. With decreased blinking, the eyes become dry, which can result in fatigue, irritation, itching, and even burning eyes. Such symptoms can also lower productivity.

It has also been shown that children are affected to a greater extent by close-up viewing of display screens associated with electronic computing devices. While viewing display screens, they blink at an even lower rates than adults do. Particularly in children, whose eyes are still developing, stressing the eyes can lead to premature myopia and short-term health effects, such as stress and headaches.

BRIEF DESCRIPTION OF THE FIGURES

The accompanying figures, where like reference numerals refer to identical or functionally similar elements throughout the separate views, form part of the specification and illustrate embodiments in accordance with the included claims.

FIG. 6 shows a pair of tables illustrating determining effectiveness scores for blink inducements in accordance with an embodiment.

Figure 1:
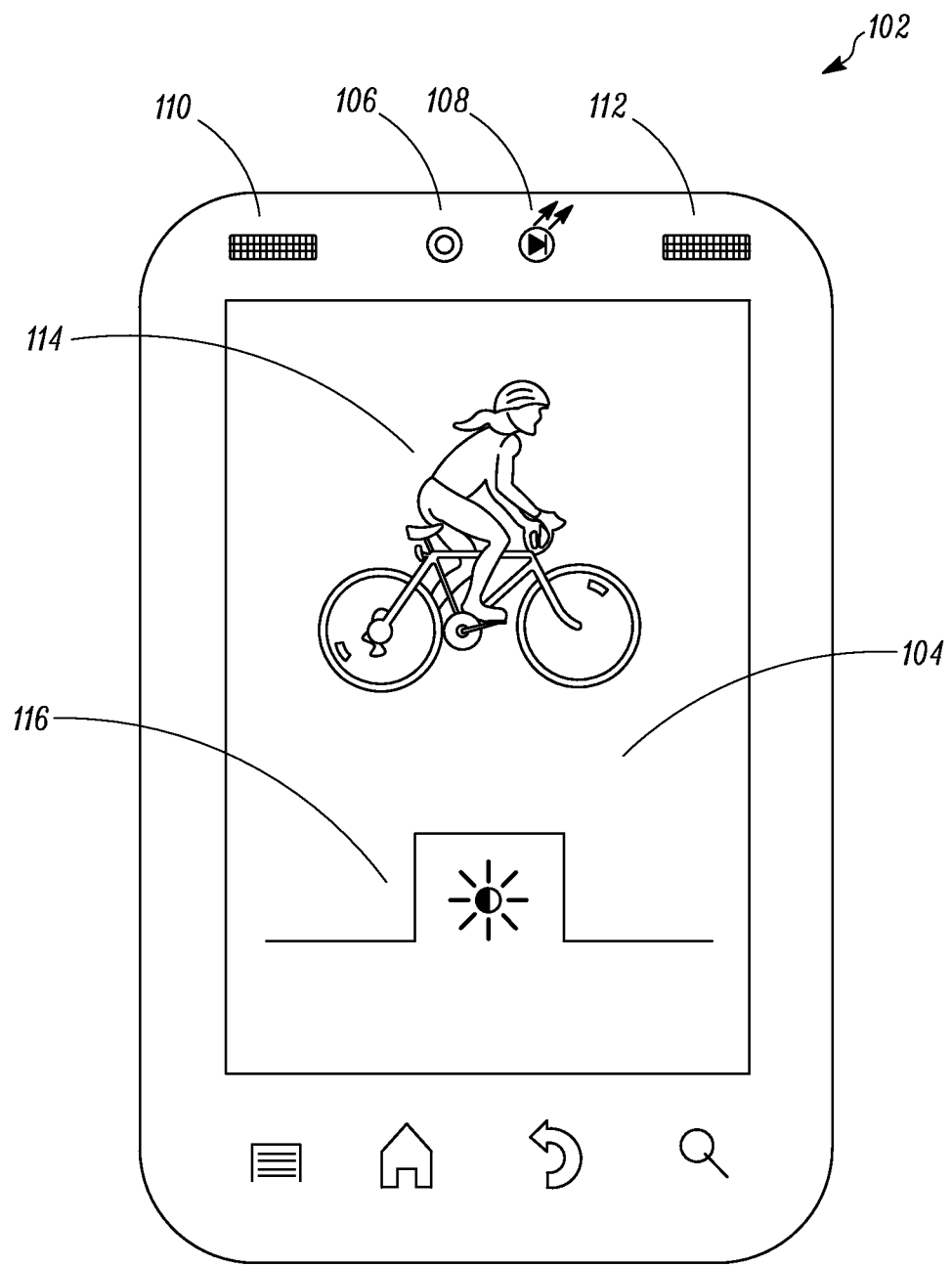
FIG. 1 is an illustration of an electronic computing device in accordance with an embodiment.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present teachings. In addition, the description and drawings do not necessarily require the order presented. It will be further appreciated that certain actions and/or steps may be described or depicted in a particular order of occurrence while those skilled in the art will understand that such specificity with respect to sequence is not actually required.

The apparatus and method components have been represented, where appropriate, by conventional symbols in the drawings, showing only those specific details that are pertinent to understanding the embodiments of the present teachings so as not to obscure the disclosure with details that will be readily apparent to those of ordinary skill in the art having the benefit of the description herein.

DETAILED DESCRIPTION

Generally speaking, pursuant to various embodiments described herein, the present disclosure provides a method and apparatus for managing blinking by inducing a user of an electronic computing device to blink at an induced blink rate that is dependent, either directly or indirectly, upon an uninduced blink rate for the user. For a particular embodiment, the electronic computing device presents blink inducements to the user based upon a determination of the effectiveness of the blink inducements at getting the user to blink.

In accordance with the teachings herein, a method performed by an electronic computing device for managing blinking includes detecting blinking of a user of the electronic computing device. The method further includes determining an uninduced blink rate for the user from the detected blinking and inducing the user to blink based on the uninduced blink rate.

Also in accordance with the teachings herein, a method performed by an electronic computing device for managing blinking includes presenting a user of the electronic computing device with a blink inducement of a plurality of blink inducements. The method additionally includes determining whether the user blinked in response to presenting the blink inducement and presenting the blink inducement again based on the determination of whether the user blinked in response to presenting the blink inducement.

Further in accordance with the teachings herein is an electronic computing device configured to manage blinking. The electronic computing device includes at least one blink sensor module, configured to receive blink sensor data, and at least one blink inducement module, configured to present a plurality of blink inducements. The electronic computing device also includes a processing element operatively coupled to the at least one blink sensor module and the at least one blink inducement module. The processing element is configured to present a blink inducement from the plurality of blink inducements using the blink inducement module and to determine, based on the blink sensor data received by the at least one blink sensor module, whether a user of the electronic computing device blinked in response to the presented blink inducement. The processing element is additionally configured to present the blink inducement again based on the determination of whether the user blinked in response to the presented blink inducement.

For one embodiment, the at least one blink sensor module includes a camera, and/or the at least one blink inducement module includes a display screen. In a further embodiment, the processing element is also configured to determine, based on the blink sensor data received by the at least one blink sensor module, an uninduced blink rate for the user and to present, using the blink inducement module, the user with additional blink inducements from the plurality of blink inducements at a presented inducement rate based on the determined uninduced blink rate.

As used herein, a "blink sensor module" is defined as one or more hardware components of an electronic computing device that are configured to detect or perform a function necessary for detecting a user of the electronic computing device blinking. A "blink inducement module" is defined herein as one or more hardware components of an electronic computing device that are configured to present one or more blink inducements to a user of the electronic computing device. A "blink inducement" is defined herein as a stimulus or stimuli presented to a user of an electronic computing device for the purpose of evoking a blink reaction in the user.

Referring to the drawings, FIG. 1 shows an electronic computing device 102, also referred to herein as an "electronic device" or simply as a "device," implementing embodiments in accordance with the present teachings. Specifically, the device 102 represents a smartphone that includes a display screen 104, a camera 106, a flash module 108, and left 110 and right 112 stereo speakers. While two stereo speakers 110, 112 are shown for the device 102, other devices consistent with the teachings herein may have different numbers of speakers, including devices with no speakers or only a single monaural speaker.

Shown on the display screen 104 is an image 114 of a cyclist which serves as a general representation of anything a user of the device 102 might be viewing or interacting with on the display screen 104, such as a document, a webpage, a movie, or a game. An image 116 represents a brightness and/or a contrast of the display screen 104 being changed, where the brightness and/or the contrast of the display screen 104 is adjustable. For example, the brightness of the display screen 104 is momentarily increased and then returned to its previous value. "Spiking" the brightness in this manner is one way to induce a user viewing the display screen 104 to blink.

A user blinking in response to a presented blink inducement can be a reflex reaction or a conditioned response. In a first example of a reflex reaction, the device 102 flashes the flash module 108 at one tenth of its full flash capacity to induce a user to blink. As the user is viewing the display screen 104, the user sees the flash and blinks as a reflex reaction. In a second example of a reflex reaction, the speakers 110, 112 momentarily play a shrill sound. In response to the sound, the user blinks as a reflex reaction.

In an example of a conditioned response, the device 102 uses the speakers 110, 112 to play a tone each time it uses the flash module 108 to induce a user to blink as a reflex reaction. The device 102 uses the speakers 110, 112 and the flash module 108 together to condition the user to blink in response to a blink inducement presented by the speakers 110, 112 alone. Either gradually or abruptly, the device 102 ceases to use the flash module 108 at a future time when inducing the user to blink. Instead, the device 102 only plays the tone, and the user blinks in response to hearing the tone as a conditioned response. Over time, the conditioning of the user may weaken to the point where the user no longer blinks consistently when hearing the tone. The conditioning may be reinforced by the device 102 again using the flash module 108 when playing the tone. Alternatively, the device 102 may recondition the user to blink in response to hearing the tone by using another component to present a reflex-inducing stimulus when playing the tone.

While a smartphone is shown at 102, no such restriction is intended or implied as to the type of electronic computing device to which these teachings may be applied. Other suitable devices include, but are not limited to: phablets; tablets; personal digital assistants (PDAs); portable media players (e.g., MP3 players); electronic book readers; personal global-positioning-system (GPS) receivers; desktop and laptop computers; and wearable electronic computing devices, such as devices worn with a wristband or armband. As used herein, an electronic computing device is an apparatus that operates by manipulating the flow of electrons using one or more semiconductors and that includes a processing element configured to perform functionality consistent with the present teachings.

Figure 2:
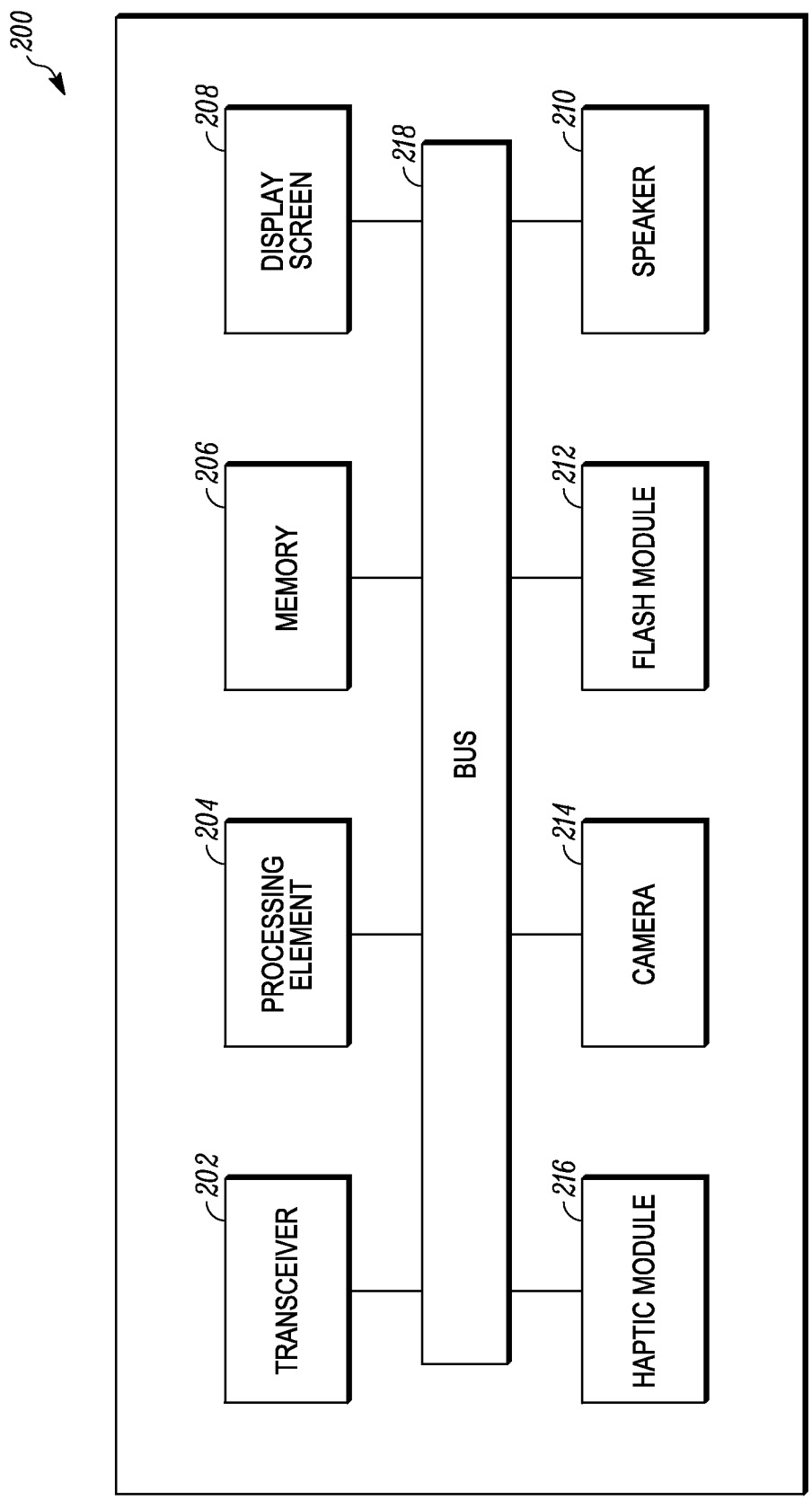
FIG. 2 is a block diagram of components of an electronic computing device in accordance with an embodiment.

FIG. 2 shows a block diagram 200 illustrating some hardware components of an electronic computing device in accordance with embodiments of the present teachings. For one embodiment, the block diagram 200 represents some of the components of the device 102. Specifically, the block diagram 200 shows a transceiver 202, a processing element 204, memory 206, a display screen 208, a speaker 210, a flash module 212, a camera 214, and a haptic module 216, which are all operatively interconnected by a bus 218.

A limited number of hardware components 202, 204, 206, 208, 210, 212, 214, 216 and 218 are shown in the diagram 200 for ease of illustration, but other embodiments may include a lesser or greater number of such components in an electronic computing device. Moreover, other hardware components needed for a commercial embodiment of an electronic computing device that incorporates the components shown in the diagram 200 are omitted from FIG. 2 for clarity in describing the enclosed embodiments. Further, these hardware components work in conjunction with each other, and in some instances with one or more software modules, to perform their intended functionality in accordance with the embodiments described herein.

We now turn to a brief description of the hardware components within the block diagram 200. In general, the processing element 204 is configured with functionality in accordance with embodiments of the present disclosure as described in detail below with respect to the remaining figures. "Adapted," "operative," "capable" or "configured," as used herein, means that the indicated components are implemented using one or more hardware elements, such as one or more operatively coupled processing cores, memory elements, and interfaces, which may or may not be programmed with software and/or firmware, as the means for the indicated components to implement their desired functionality. Such functionality is supported by the other hardware shown in FIG. 2, including the device components 202, 206, 208, 210, 212, 214, 216, and 218.

The processing element 204, for instance, includes arithmetic logic and control circuitry necessary to perform the digital processing, in whole or in part, for the electronic device 102 to manage blinking in accordance with described embodiments of the present teachings. For one embodiment, the processing element 204 represents a primary microprocessor, also referred to as a central processing unit (CPU), of the electronic device 102. For example, the processing element 204 can represent an application processor of a smartphone. In another embodiment, the processing element 204 is an ancillary processor, separate from the CPU, wherein the ancillary processor is dedicated to providing the processing capability, in whole or in part, needed for the device components of the block diagram 200 to perform at least some of their intended functionality.

The memory 206 provides storage of electronic data used by the processing element 204 in performing its functionality. For example, the processing element 204 can use the memory 206 to store and/or cache data. In one embodiment, the memory 206 represents random access memory (RAM). In other embodiments, the memory 206 represents volatile or non-volatile memory. For a particular embodiment, a portion of the memory 206 is removable. For example, the processing element 204 can use high-speed RAM to cache data while it uses a micro secure digital (microSD) card to store data.

The display screen 208 displays visual images for viewing by one or more users of an electronic device represented by the block diagram 200. For some embodiments, static and/or dynamic images displayed by the display screen 208 serve as a source of entertainment or productivity for a user. For example, a user might use an electronic computing device with the display screen 208 to watch videos or write a report. In other embodiments, images displayed by the display screen 208 provide a means by which a user can operate an electronic device. Where the display screen 208 of an electronic device functions as an input device, such as a touchscreen, for example, an operating system allows a user to interact with the display screen 208 to manipulate displayed icons and menus to operate the electronic device.

For some described embodiments, the display screen 208 is configured as a blink inducement module to present blink inducements that can elicit a blink response from a user either as a reflex reaction or a conditioned response. Ways in which an electronic device can use the display screen 208 to induce a user to blink include, but are not limited to, momentarily increasing a brightness of the display screen 208, momentarily causing the display screen 208 to pulse, momentarily causing the display screen 208 to go dark, momentarily inverting colors and/or contrasts appearing on different portions of the display screen 208, momentarily changing a focus and/or a resolution of the display screen 208, momentarily presenting motion on the display screen 208 directed toward the user, and/or momentarily changing an image being displayed on the display screen 208.

In additional embodiments, the display screen 208 is configured to momentarily display a message as a blink inducement or in conjunction with a blink inducement. To induce a user to blink in a first example, the display screen 208 flashes a message requesting that the user blink. In a second example, the display screen 208 flashes the message while the speaker 210 plays a tone to induce the user to blink.

The speaker 210, which for an embodiment represents the stereo speakers 110, 112, can also be configured as a blink inducement module to present blink inducements that elicit blinking from a user either as a reflex reaction or a conditioned response. For example, the speaker 210 emits a sound that is of sufficient volume and/or pitch to induce a user to blink. In one embodiment, a device uses the camera 214 to monitor the user's response to the emitted sound. If the device determines that the user did not blink in response to the sound, then the device adjusts the volume and/or pitch of the sound until the user does blink. In further embodiments, the speaker 210 also plays audible blink-request messages. In one embodiment, blink-request messages are prerecorded. In another embodiment, a text-to-speech module is used to play over the speaker 210 a blink-request message being displayed by the display screen 208.

For some embodiments, a device represented by the block diagram 200 uses the flash module 212 as a blink inducement module. To induce a user to blink, the device presents the user with one or more flashes. In a particular embodiment, the timing and/or intensity of the flashes can be varied to more effectively induce the user to blink.

The haptic module 216 is configured to induce a user to blink by providing the user with a tactile stimulus. For example, the haptic module 216 is a small motor included in the device 102 that is controlled by the processing element 204 to rotate an unbalanced weight to cause vibrations. The vibrations can be changed by altering the speed at which and the duration for which the motor runs. The device 102 might use a strong vibration to induce the user to blink in a reflex reaction. The device 102 might also use a relatively weaker vibration, or pattern of vibrations, to induce the user to blink as a conditioned response.

In some instances, the device 102 uses the haptic module 216 to induce blinking when using the speaker 210 or the flash module 212 to induce blinking could potentially be ineffective or distracting to individuals other than the user located near the device 102. In one embodiment, the device 102 uses the haptic module 216 to induce blinking when the user places the device 102 in a silent mode after entering a library. In another embodiment, the device 102 uses the haptic module 216 to induce blinking when the device determines, using a microphone, for example, that a noisy environment would make using the speaker 210 to induce blinking less effective. In a further embodiment, the device 102 uses the haptic module 216 to induce blinking when the device determines, using the camera 214, for example, that a bright environment would make using the flash module 212 to induce blinking less effective.

As described herein, inducing a user to blink includes presenting the user with a set of blink inducements. A "set" is defined so that it may include only a single element in some embodiments and also include multiple elements in other embodiments. For example, to induce a user to blink repeatedly, a device might present the user with a single blink inducement multiple times or present multiple blink inducements once each. In one embodiment, the device induces a user to blink by presenting different blink inducements with each blink inducement being presented a different number of times. In a further embodiment, the frequency with which the device presents a blink inducement depends upon an effectiveness of the blink inducement in getting the user to blink.

The camera 214 is used by an electronic device to capture image data. In some embodiments, the device uses the camera 214 as a blink sensor module Image data captured by the camera 214 is used to determine whether a user blinked in response to a presented blink inducement. For example, the processing element 204 receives image data captured by the camera 214 and processes the image data to identify visual markers. The processing element 204 then compares the visual markers against a database of reference markers that are associated with reference images of open eyes and closed eyes. If the processing element 204 can match a sufficient number of the visual markers to the reference markers, then the processing element 204 can determine from the captured image data whether the user blinked.

For example, a blink inducement module presents a user with a blink inducement. Immediately after the blink inducement is presented, the camera 214, being used as a blink sensor module, captures image data from the user. From the captured image data, the processing element 204 identifies twelve visual markers. Of the twelve visual markers, the processing element 204 matches eight markers to reference markers for closed eyes, matches one visual marker to reference markers for open eyes, and is unable to match the remaining three visual markers to any reference markers. A ratio of a number of visual markers matched to reference markers for closed eyes to a total number of visual markers is 0.67. A ratio of a number of visual markers matched to reference markers for open eyes to a number of visual markers matched to reference markers for closed eyes is 0.13. Given that the first ratio is greater than a first threshold ratio and the second ratio is less than a second threshold ratio, the processing element 204 determines the user blinked in response to the presented blink inducement.

In an alternate embodiment, the processing element 204 processes a series of "frames" of image data captured by the camera 214 during a time duration after a blink inducement is presented. The processing element 204 processes each frame, and for each frame determines a statistical likelihood that a user's eyes are closed in that frame. If the statistical likelihood exceeds a threshold likelihood, then the processing element 204 determines the user's eyes were closed. If the processing element 204 determines the user's eyes were closed for one or more frames of the series of frames, then the processing element 204 determines the user blinked in response to the presented blink inducement.

The device also uses the camera 214 to determine when the user blinks on his or her own, not in response to a blink inducement presented by the device. Natural blinking, which is not in response to presented blink inducements, is referred to herein as "uninduced blinking." Blinking that is in response to presented blink inducements is referred to herein as "induced blinking." For an embodiment, the device determines when the user blinks by processing a continuous series of image-data frames captured by the camera 214. If the processing element determines there was a presented blink inducement immediately preceding a detected blink, then the detected blink is identified as an induced blink, otherwise the detected blink is identified as an uninduced blink. The camera 214 captures the frames of image data over time at a rate that is inversely proportional to a blink duration to ensure a blink is not begun and completed without the camera 214 capturing image data while the blink was in progress.

For some embodiments, the processing element 204 also processes image data to determine characteristics of a user other than if the user is blinking. In a particular embodiment, the processing element 204 processes image data captured by the camera 214 to determine if a user is a child or an adult. For example, a database of reference markers associated with people in different age groups might be used by the processing element 204 in making a determination of whether the user is a child. The database may be stored locally on a device that includes the processing element 204, using the memory 206, or it may be stored remotely on another device and accessed using the transceiver 202.

The transceiver 202 is configured to support communications to and from an electronic computing device. In one embodiment, the transceiver 202 is a cellular transceiver 202. The electronic computing device uses a cellular network to receive data from other devices with similar capabilities. Cellular networks can use any wireless technology that, for example, enables broadband and Internet Protocol (IP) communications including, but not limited to, $3^{rd}$ Generation (3G) wireless technologies such as CDMA2000 and Universal Mobile Telecommunications System (UMTS) networks or $4^{th}$ Generation (4G) wireless networks such as LTE and WiMAX.

In another embodiment, the transceiver 202 is a WLAN transceiver that allows the electronic computing device to access the Internet using standards such as Wi-Fi. The WLAN transceiver 202 allows the electronic computing device to send and receive radio signals to and from similarly equipped electronic devices using a wireless distribution method, such as a spread-spectrum or orthogonal frequency-division multiplexing (OFDM) method. For some embodiments, the WLAN transceiver 202 uses an IEEE 802.11 standard to communicate with other electronic devices in the 2.4, 3.6, 5, and 60 GHz frequency bands. In a particular embodiment, the MILAN transceiver 202 uses Wi-Fi interoperability standards as specified by the Wi-Fi Alliance to communicate with other Wi-Fi certified devices.

In addition to an electronic computing device using the transceiver 202 to access remote databases to aid the processing element 204 in determining user characteristics and whether a user blinked, the transceiver 202 is configured for use by the electronic computing device in updating its programming. The electronic computing device receives new algorithms and/or updates to old algorithms and/or programs used by the device to perform functionality in accordance with embodiments described herein.

For some embodiments, a battery (not shown) represents a power source that supplies electric power to the device components 202, 204, 206, 208, 210, 212, 214, 216, 218, as needed, during the course of their normal operation. The power is supplied to meet the individual voltage and load requirements of the device components 202, 204, 206, 208, 210, 212, 214, 216, 218 that draw electric current. For an embodiment, the battery also powers up and powers down a device using one or more of the device components 202, 204, 206, 208, 210, 212, 214, 216, 218. For a particular embodiment, the battery is a rechargeable power source. A rechargeable power source for a device is configured to be temporarily connected to another power source external to the device to restore a charge of the rechargeable power source when it is depleted or less than fully charged. In another embodiment, the battery is simply replaced when it no longer holds sufficient charge.

Figure 3:
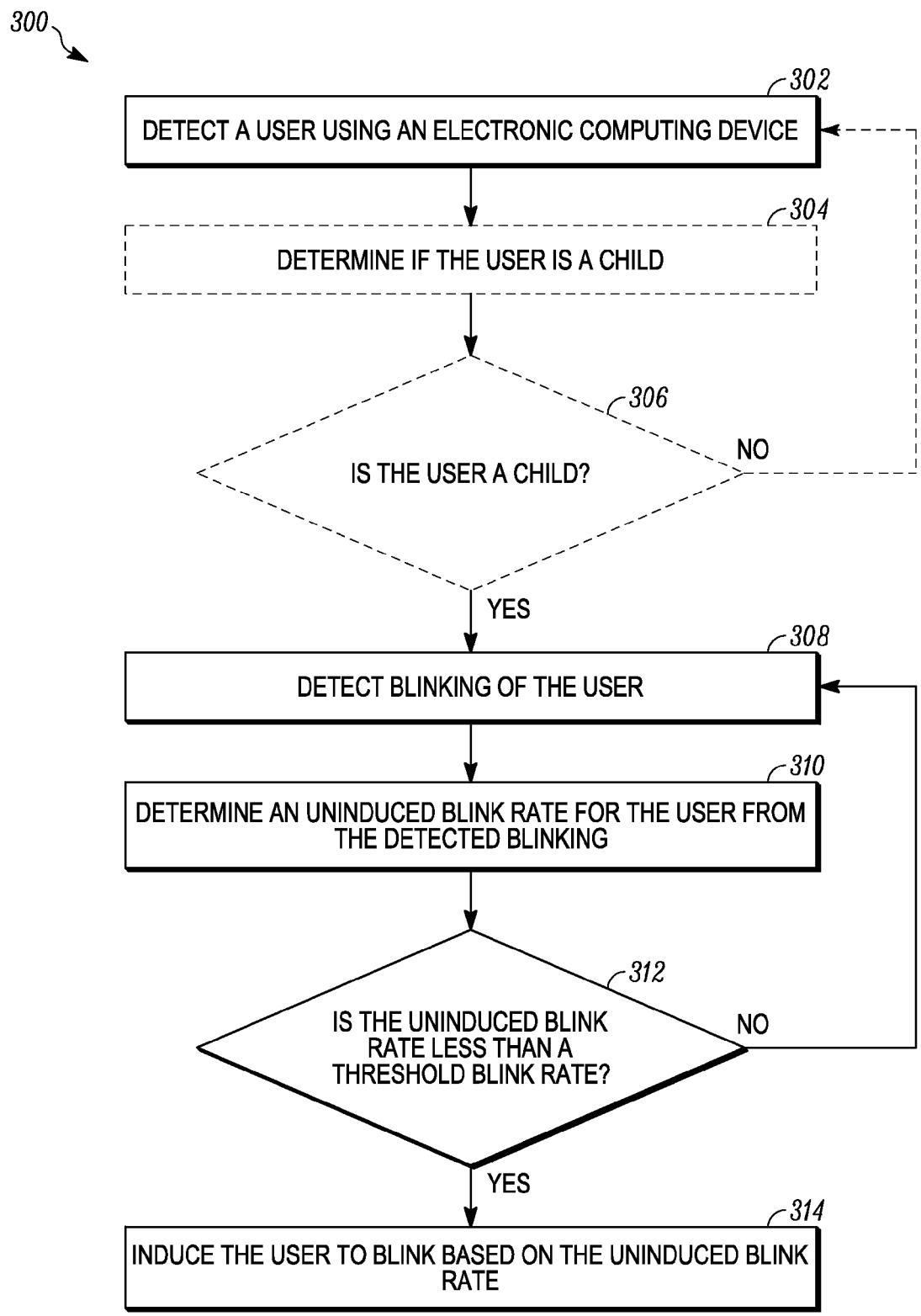
FIG. 3 is a logical flowchart depicting a method for inducing a user of an electronic computing device to blink in accordance with an embodiment.

We turn now to a detailed description of the functionality of the device components shown in FIGS. 1 and 2, in accordance with the teachings herein and by reference to the remaining figures. FIG. 3 is a logical flow diagram illustrating a method 300 performed by a device, taken to be device 102 for purposes of this description, for inducing a user of the device to blink. Specifically, the device 102 detects 302 a user. In a first embodiment, the camera 106 detects the user positioned in front of the device 102. In a second embodiment, the device 102 detects user interaction through an input device, such as when the display screen 104 is being used as a touchscreen. In a third embodiment, the device 102 detects that it is being gripped by touch sensors located at different positions on or within a housing of the device 102.

For one embodiment, the device 102 performs the optional operation, depicted by the use of broken lines, of determining 304 whether the user is a child. If the device 102 determines 306 the user is a child, then the device 102 continues to enforce blinking for the child. If the device 102 determines 306 the user is not a child, then the device 102 does not enforce blinking for the user. Upon detecting 302 a new user, the device 102 again determines 304 if the user is a child. For another embodiment, the device 102 enforces blinking for all users, not just children. In a further embodiment, the device 102 is selectively set to enforce blinking for a user. In a first instance, an owner of the device 102 sets the device 102 to enforce blinking before allowing a child to operate the device 102. In a second instance, the device 102 enforces blinking based on login preferences. When a first user logs into the device 102 using a first account, the device enforces blinking for the first user. When a second user logs into the device 102 using a second account, the device does not enforce blinking.

Having detected 302 a user using the device 102 for whom blinking will be enforced, the device 102 detects 308 the user blinking. In a first embodiment, the camera 106 and processing element 204 of device 102 detect the user blinking as described above in reference to FIG. 2. In a second embodiment, an electronic computing device uses a blink sensor module that includes a photodetector, such as a photodiode, to detect a user blinking.

For a wearable electronic computing device, such as a device worn with eyeglass frames, a light-emitting diode (LED) is positioned near one or both of a user's eyes. The LED emits infrared light at a frequency below the visible spectrum so as to go unnoticed by the user wearing the eyeglass frames. A photodetector is placed to receive light emitted from the LED and reflected by the user's eyes. The outside of the user's eyelids have a different optical reflectivity than the user's eyes. How light is absorbed, reflected, and scattered from the skin of the eyelids is different than it is for the eyes. The skin of the eyelids is rough, dry, and one-dimensional, whereas the eyes are smooth, wet, and multi-dimensional by comparison. The eyes are multidimensional in the sense that there are multiple structures within the eyes from which light is reflected, namely the cornea, iris, pupil, lens, and retina. The processing element 204 is programmed to detect specific differences in the reflected light captured by the photodetector to determine if the light was reflected by the user's eyes or the user's eyelids. If the reflected light that is detected matches a signature for the user's eyelids, then the device 102 determines the user is blinking.

Using one or more blink sensor modules, the device 102 determines 310 an uninduced blink rate for the user from detected blinking. That is the device 102 detects multiple uninduced blinks over a time period. By dividing a number of detected uninduced blinks by the time period, the device 102 determines 310 the uninduced blink rate for the user. This is the rate at which the user blinks while no blink inducements are being presented by the device 102. The device 102 then compares the uninduced blink rate to a threshold blink rate.

For some embodiments, the threshold blink rate represents a target blink rate, a blink rate that is considered normal based, for example, on medical studies. For instance, the threshold blink rate might be ten blinks per minute. In another embodiment, the threshold blink rate is different based on whether the device 102 determines if it is being used by a child or an adult. Normal blinks rates differ between children and adults, with children having lower blink rates. The device 102 might set the threshold blink rate to five blinks per minute, for example, if a child is using the device 102, or to ten blinks per minute if an adult is using the device 102. While five and ten blinks per minute are indicated here for explanatory purposes, no such restriction is implied with regard to the threshold blink rate when the present teachings are applied in practice. A threshold blink rate, for example, might be as low as two blinks per minute or as high as twenty blinks per minute.

In one embodiment, the blink threshold is set below an average blink rate determined for a statistical sample of individuals. In conducting studies on the blinking of healthy individuals, for example, a distribution of blink rates represents a normal distribution with a given mean and standard deviation. The device 102 sets the threshold blink rate not at the mean, but rather one standard deviation below the mean. If the device 102 determines 312 the uninduced blink rate is below the threshold blink rate, then the device 102 induces 314 the user to blink. In this way, the device only induces its user to blink when the user's uninduced blink rate is below a natural blink rate for 84 percent of the population, yet is still above a natural blink rate for the other 16 percent of the population.

Figure 4:
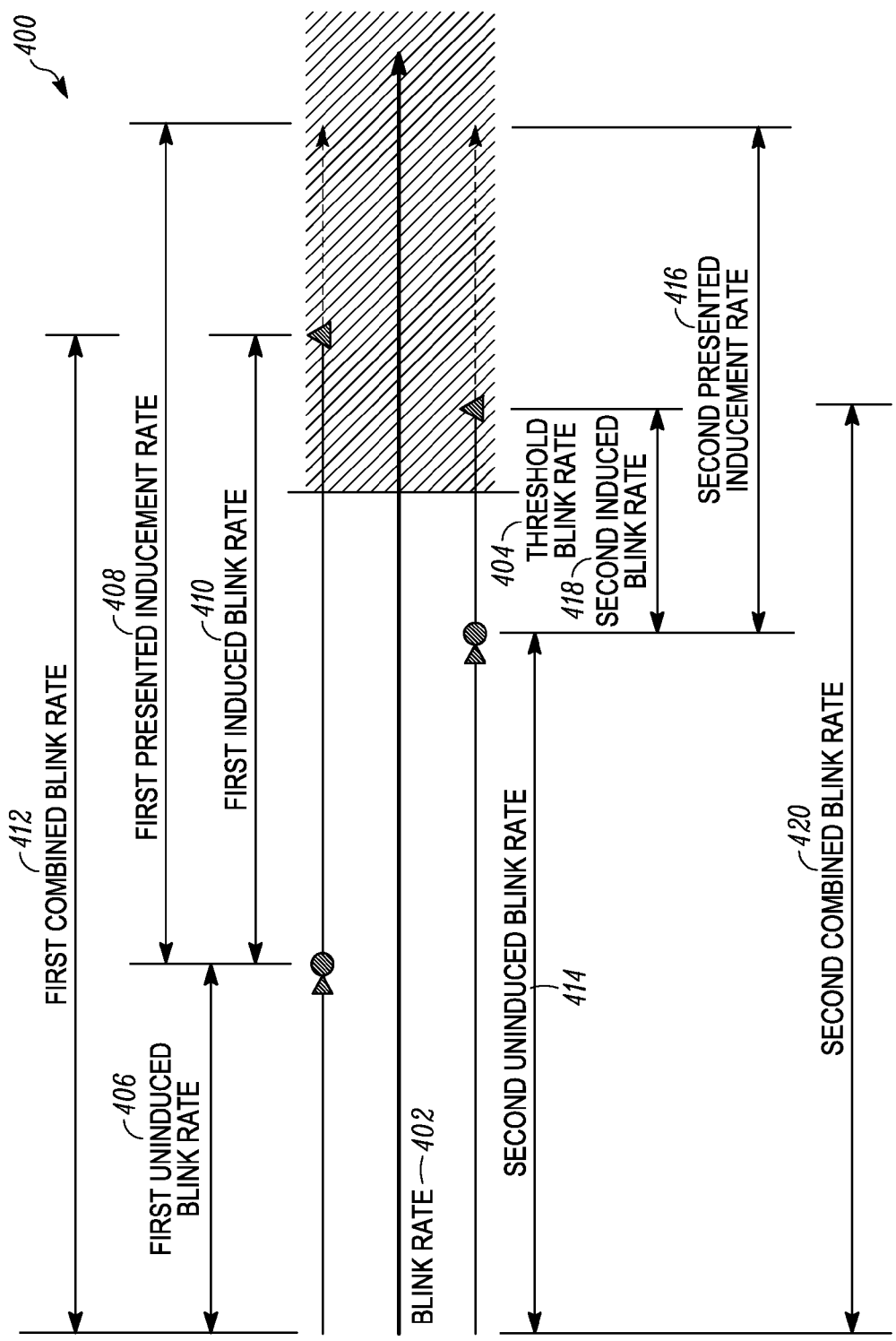
FIG. 4 is a line diagram illustrating a dependence of a presented inducement rate upon an uninduced blink rate in accordance with an embodiment.

Turning to FIG. 4, the method 300 is described in greater detail. FIG. 4 shows a line diagram 400 illustrating a dependence of a presented inducement rate upon an uninduced blink rate and/or a combined blink rate. The diagram 400 includes a line 402 representing different blink rates, with blink rates increasing from left to right. Intersecting the line 402 is a line 404, which represents a threshold blink rate. Blink rates higher than the threshold blink rate 404 are shown shaded.

For a first user, the device 102 detects a given number of uninduced blinks over a time interval. By dividing the detected number of uninduced blinks by the time interval, the device 102 determines a first uninduced blink rate 406 for the first user. As indicated by the diagram 400, the first uninduced blink rate 406 is less than the threshold blink rate 404. To increase the rate at which the first user blinks, the device 102 presents the first user with blink inducements from a set of blink inducements. The device 102 presents the blink inducements to the first user at a first presented inducement rate 408. A presented inducement rate is defined herein as a number of blink inducements a device presents per unit time.

In one embodiment, the presented inducement rate is greater than or equal to a difference between the threshold blink rate and the uninduced blink rate. Thus, the presented inducement rate added to the uninduced blink rate is equal to or greater than the threshold blink rate. Diagram 400 illustrates the latter case. A first presented inducement rate 408 is greater than the difference between the threshold blink rate 404 and the first uninduced blink rate 406. When the lines representing the uninduced blink rate 406 and the first presented blink rate 408 are placed end-to-end as shown, the two lines taken together, representing the addition of the two rates 406, 408, extend past the threshold blink rate 404 and into the shaded region.

In a further embodiment, the presented inducement rate is adjusted based on an induced blink rate so that the induced blink rate is greater than or equal to a difference between the threshold blink rate and the uninduced blink rate. An induced blink rate is defined herein as a number of induced blinks a user makes per unit time. This embodiment is based on the reasoning that not every blink inducement the device 102 presents is successful in inducing a user to blink. Accordingly, an induced blink rate can be less than or equal to, but not greater than, a corresponding presented inducement rate. This is reflected in the diagram 400 by a line 410 representing a first induced blink rate being shorter than the line 408 representing the first presented inducement rate. The difference in length between the two lines 408, 410 is shown dashed and represents a failure rate for the first presented inducement rate, namely, the rate at which presented inducements fail to induce the user to blink. A line 412 has a combined length of the lines 406 and 410 and represents a first combined blink rate for the first user. This is the total rate at which the first user blinks, for which both uninduced and induced blinks are considered. For this embodiment, the first presented inducement rate 408 is great enough so that despite unsuccessful blink inducements the first combined blink rate 412 is equal to or exceeds the threshold blink rate 404.

Shown in the lower half of the diagram 400 are also lines 414, 416, 418, and 420 representing a second uninduced blink rate, a second presented inducement rate, a second induced blink rate, and a second combined blink rate, respectively, for as second user or for the first user at a later time. For an embodiment, the device 102 monitors the uninduced blink rate for the user over time. This means the device 102 determines from the user's uninduced blinking, as the user continues to blink, the second uninduced blink rate 414 which supersedes the user's first uninduced blink rate 406. The device 102 then presents at least one blink inducement from the set of blink inducements at the second presented inducement rate 416, wherein the second presented inducement rate 416 is based on a difference between the threshold blink rate 404 and the second uninduced blink rate 414. The presented inducement rate has an inverse relationship with the uninduced blink rate. Because the second uninduced blink rate 414 is greater than the first uninduced blink rate 406, the second presented inducement rate 416 is less than the first presented inducement rate 408. For a particular embodiment, the presented inducement rate is zero once the uninduced blink rate is greater than the threshold blink rate. If the user is blinking naturally at a sufficient rate, there is no need to induce additional blinking.

For some embodiments, the device 102 monitors the combined blink rate for the user and adjusts the presented inducement rate based on the monitored combined blink rate. If the monitored combined blink rate increases, then the device 102 decreases the presented inducement rate. The first presented inducement rate 408, for example, is decreased to the second presented inducement rate 416 as the first uninduced blink rate 406 increases to the second uninduced blink rate 414. This is because the combined blink rate increases with the increasing uninduced blink rate. In one embodiment, the presented inducement rate decreases to zero as the uninduced blink rate increases beyond the threshold blink rate 404. If the monitored combined blink rate decreases, then the device 102 increases the presented inducement rate to compensate.

Figure 5:
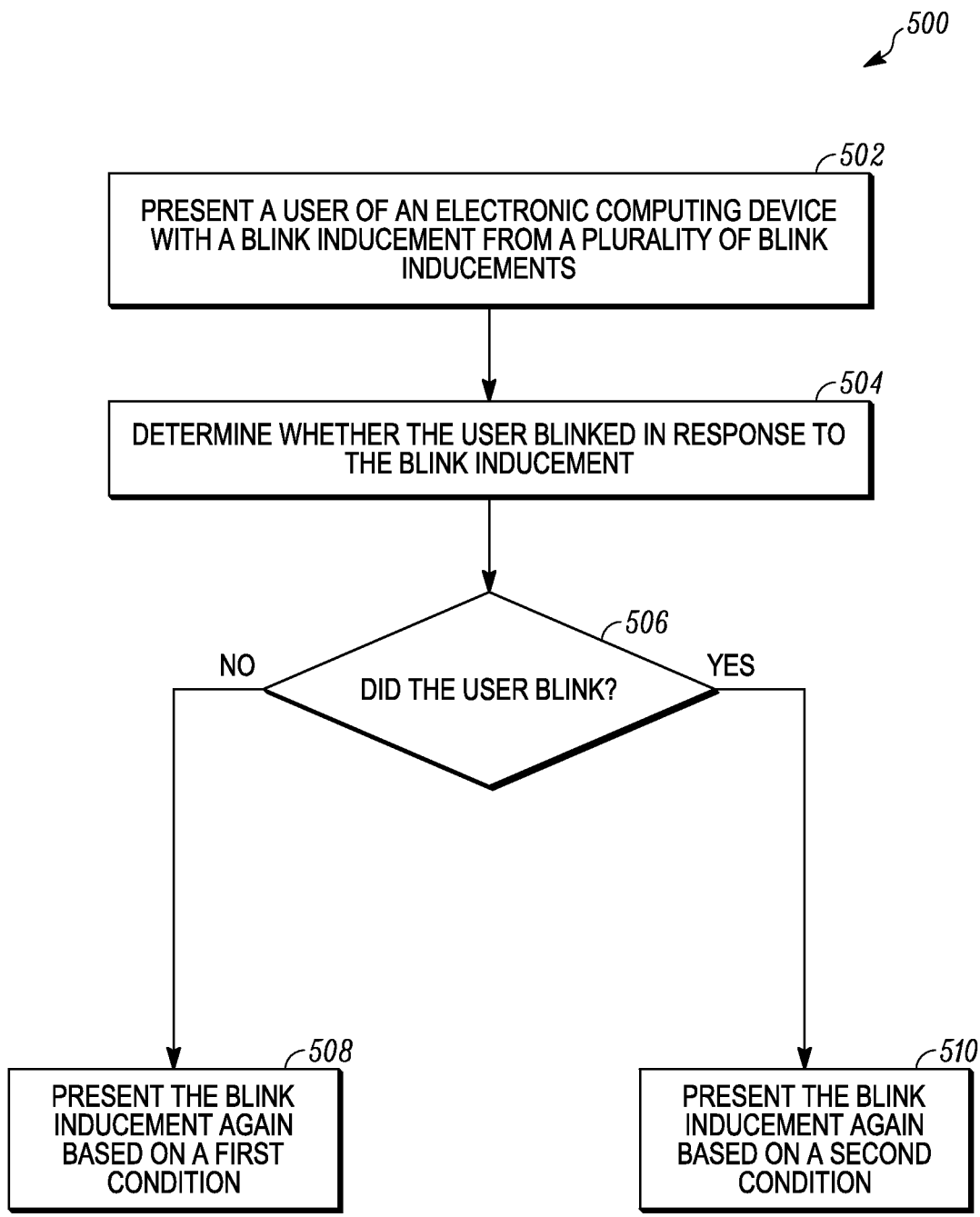
FIG. 5 is a logical flowchart depicting a method for inducing a user of an electronic computing device to blink in accordance with an embodiment.

For an embodiment, the device 102 determines the effectiveness of individual blink inducements it presents. The device 102 then uses this data to present blink inducements in a way that reduces or minimizes a difference between the presented inducement rate and the induced blink rate. FIG. 5 shows a logical flow diagram depicting a method 500 for presenting blink inducements based on whether the blink inducements are successful in inducing a user to blink.

In performing the method 500, an electronic computing device, taken for purposes of this description to be the device 102, presents 502 its user with a blink inducement from a plurality of blink inducements. The device 102 then determines 504 whether the blink inducement was successful in inducing the user to blink. If the device 102 determines 506 that the user did not blink in response to the blink inducement, then the device 102 presents 508 the blink inducement again based on a first condition. If the device determines 506 that the user did blink in response to the blink inducement, then the device 102 presents 510 the blink inducement again based on a second condition.

For one embodiment, the device 102 determines whether a user blinked in response to a first presentation of a blink inducement and presents the user with a second presentation of the blink inducement based on the determination of whether the user blinked in response to the first presentation of the blink inducement. For a particular embodiment, presenting an unsuccessful blink inducement again based on the first condition means that the unsuccessful blink inducement is presented again with a lower probability or after a greater time interval in comparison to presenting a successful blink inducement again based on the second condition.

For some embodiments, the device 102 determines an effectiveness score for a blink inducement based on whether a user blinked in response to the blink inducement. The device 102 then presents the blink inducement again based on the effectiveness score. An effectiveness score for a blink inducement, as used herein, is a quantitative measure of how successful a blink inducement is at inducing a user to blink based on one or more past presentations of the blink inducement.

FIG. 6 shows two tables 602, 604 illustrating methods of determining an effectiveness score for each of a plurality of blink inducements. For FIG. 6, as well as for the remaining figures, eight blink inducements, labeled as $I_1, I_2, I_3, I_4, I_5, I_6, I_7$, and $I_8$, represent a plurality of blink inducements for explanatory purposes. In alternate embodiments, a plurality of blink inducements may include any number of blink inducements. A device, such as device 102, determines an effectiveness score for each blink inducement based on a determination of whether the blink inducement was successful or not in inducing a user to blink each of multiple times the blink inducement was presented to the user.

Table 602 includes eight rows, one for each blink inducement, and four columns. A first column 606 identifies blink inducements. A second column 608 identifies how many times a blink inducement was presented to a user for purposes of calculating an effectiveness score for the blink inducement. Of the number of times the blink inducement was presented, the third column 610 identifies how many times the blink inducement was successful in inducing the user to blink. Tabulated in the fourth column 612 are effectiveness scores 614, 616, 618, 620, 622, 624, 626, and 628 for blink inducements $I_1, I_4, I_3, I_5, I_6, I_2, I_7$, and $I_8$, respectively.

The fourth row of table 602 indicates that the device 102 presented the blink inducement $I_5$ to the user four times. Of the four presentations, three were successful in inducing the user to blink. The device 102 determines an effectiveness score 620 of 0.75 for the blink inducement $I_5$ by dividing the three successes by the four presentations. For one embodiment, the device 102 always determines the effectiveness scores of the fourth column 612 from the last four times a blink inducement was presented. For example, when the device 102 presents the blink inducement $I_5$ again for a fifth time, the device recalculates the effectiveness score 620 based on whether the user blinked in response to only the last four times (i.e., the second, third, fourth, and fifth times) the blink inducement $I_5$ was presented. The device 102 no longer factors into the effectiveness score 620 whether the user blinked in response to the first time the blink inducement $I_5$ was presented. In different embodiments, the device may determine an effectiveness score as a rolling average in this way from any number of past presentations of a blink inducement.

In another embodiment, the device 102 weighs each presentation differently when calculating an effectiveness score for a blink inducement. For example, the device 102 might give more weight to more recent presentations of a blink inducement. Allowing a random variable $x_n$ to assume a value of zero if a user fails to blink in response to an $n^{th}$ presentation of a blink inducement and to assume a value of one if the user does blink in response to the $n^{th}$ presentation of the blink inducement, an effectiveness score for the blink inducement can be calculated using the expression:

$$0.1x_1 + 0.2x_2 + 0.3x_3 + 0.4x_4. \tag{1}$$

Using the preceding expression, the effectiveness score for the blink inducement $I_5$ would be 0.9, 0.8, 0.7, or 0.6 depending upon whether the one time the user failed to blink was in response to the first, second, third, or fourth presentation of the blink inducement $I_5$, respectively.

Table 604 also includes eight rows and four columns 630, 632, 634, 636 with a similar arrangement to table 602. The fourth column 636 shows eight effectiveness scores 638, 640, 642, 644, 646 648 650, 652, one for each blink inducement indicated in the first column 630 of the table 604. The second column 632 shows that the device 102 determines each effectiveness score based on a different number of presentations. For an embodiment, the device 102 presents more effective blink inducements more often. Thus, more effective blink inducements generally have a greater number of total presentations as compared to blink inducements with lower effectiveness scores. As shown in table 604, the device 102 determines an effectiveness score for each blink inducement as a ratio of the number of times the blink inducement was successful in inducing a user to blink, which is indicated in the third column 634, to the number of times the blink inducement was presented, which is indicated in the second column 632. In alternate embodiments, the device 102 weighs separate presentations of a blink inducement differently in determining an effectiveness score.

In some embodiments for which a plurality of blink inducements includes at least two blink inducements, the device 102 presents a user with a first and a second blink inducement and determines whether the user blinked in response to the first and second blink inducement. The device 102 determines an effectiveness score for each of the first and second blink inducements based on whether the user blinked in response to the presentations of first and second blink inducement. The device 102 then compares the two effectiveness scores to determine which is greater. In one embodiment, the device 102 selects the first blink inducement to present again with a greater statistical likelihood than selecting the second blink inducement to present again when the effectiveness score for the first blink inducement is greater than the effectiveness score for the second blink inducement.

Figure 7:
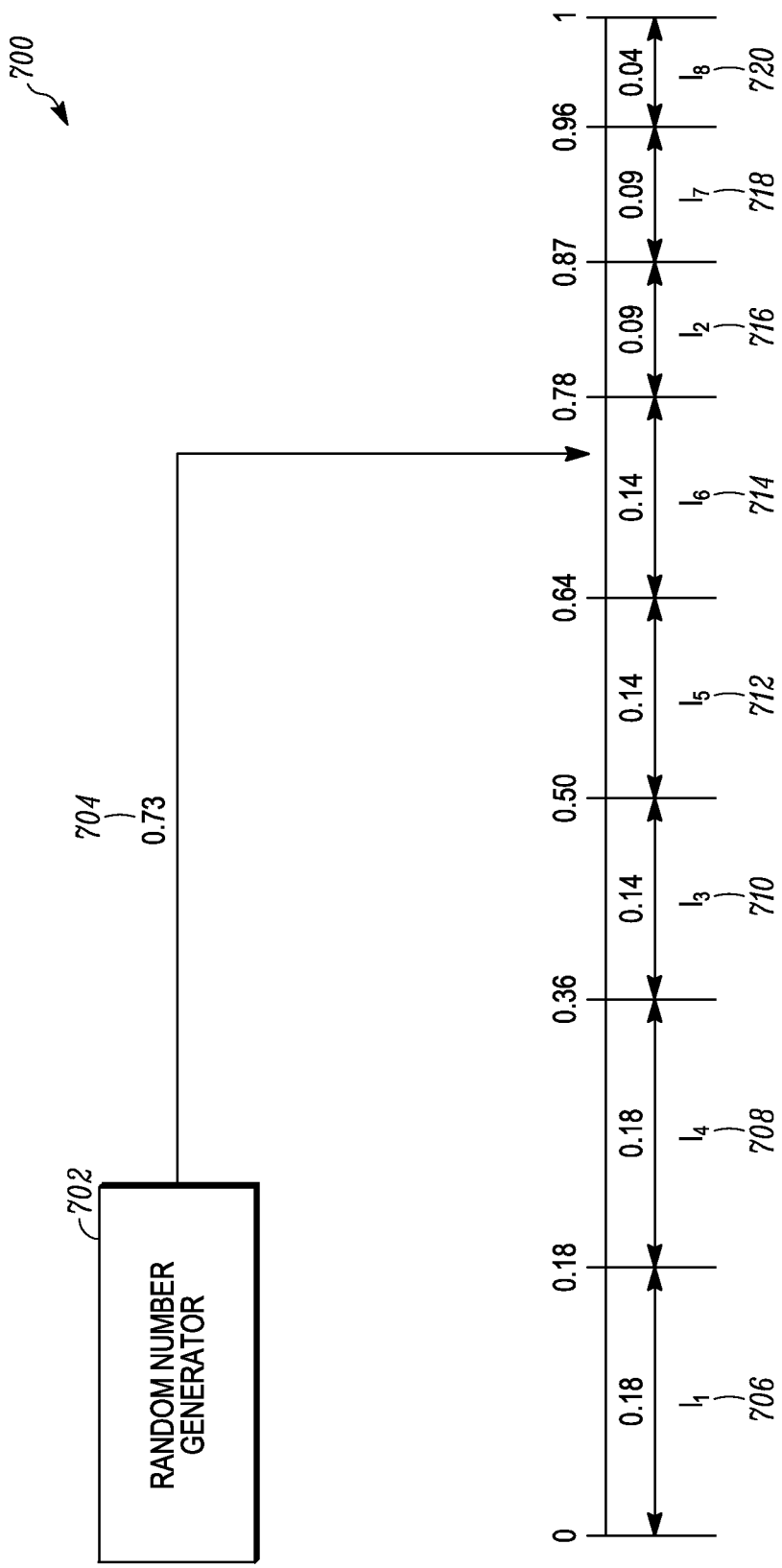
FIG. 7 is a schematic diagram illustrating a method for selecting a blink inducement in accordance with an embodiment.

FIG. 7 shows a schematic diagram 700 illustrating a method for selecting a blink inducement from a plurality of blink inducements with a statistical dependence upon the effectiveness scores for the blink inducements. In particular, the diagram 700 shows eight blink inducements 706, 708, 710, 712, 714 716, 718, 720, which are the same blink inducements shown in table 602 with the individual effectiveness scores 614, 616, 618, 620, 622, 624, 626, and 628. The effectiveness scores 614, 616, 618, 620, 622, 624, 626, 628 are normalized as shown in FIG. 7 to span an interval from zero to one when placed end-to-end. Blink inducements with relatively large effectiveness scores, such as the blink inducement $I_1$ 706, span greater portions of the interval as compared to blink inducements with relatively small effectiveness scores, such as the blink inducement $I_8$, which span lesser portions of the interval. The blink inducement $I_1$ 706 spans a range of 0.18, whereas the blink inducement $I_8$ 720 spans a range of 0.04.

A random number generator 702, which for an embodiment is functionality included within the processing element 204, generates a random number 704 with a value between zero and one. For explanatory purposes, the random number 704 is assumed to have a value of 0.73. The value of the random number 704 falls within a range of the interval from 0.64 to 0.78 spanned by the blink inducement $I_6$ 714. Therefore, the device 102 selects the blink inducement $I_6$ 714 as the next blink inducement to present to a user. After presenting the blink inducement $I_6$ 714, the device 102 determines whether the user blinked in response to the presentation and recalculates an updated effectiveness score for the blink inducement $I_6$ 714. Given the updated effectiveness score for the blink inducement $I_6$ 714, the device 102 then again renormalizes all the effectiveness scores to span the interval from zero to one and generates another random number to determine which blink inducement will be selected next. Any blink inducement has the potential of being selected with any iteration of this process, but blink inducements with higher effectiveness scores are selected with a greater statistical likelihood than blink inducements with lower effectiveness scores.

Figure 8:
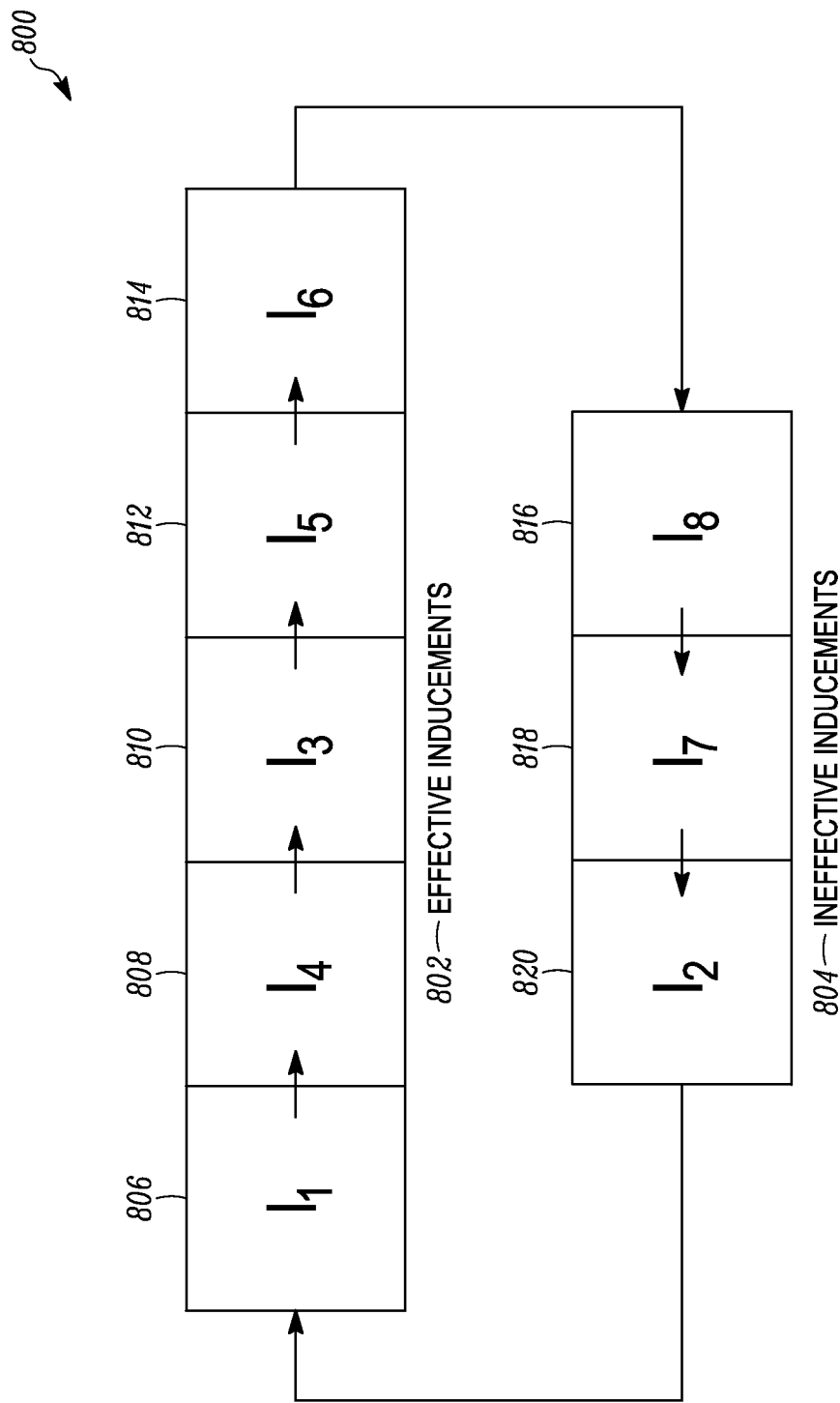
FIG. 8 is a schematic diagram illustrating a method for selecting a blink inducement in accordance with an embodiment.
Figure 9:
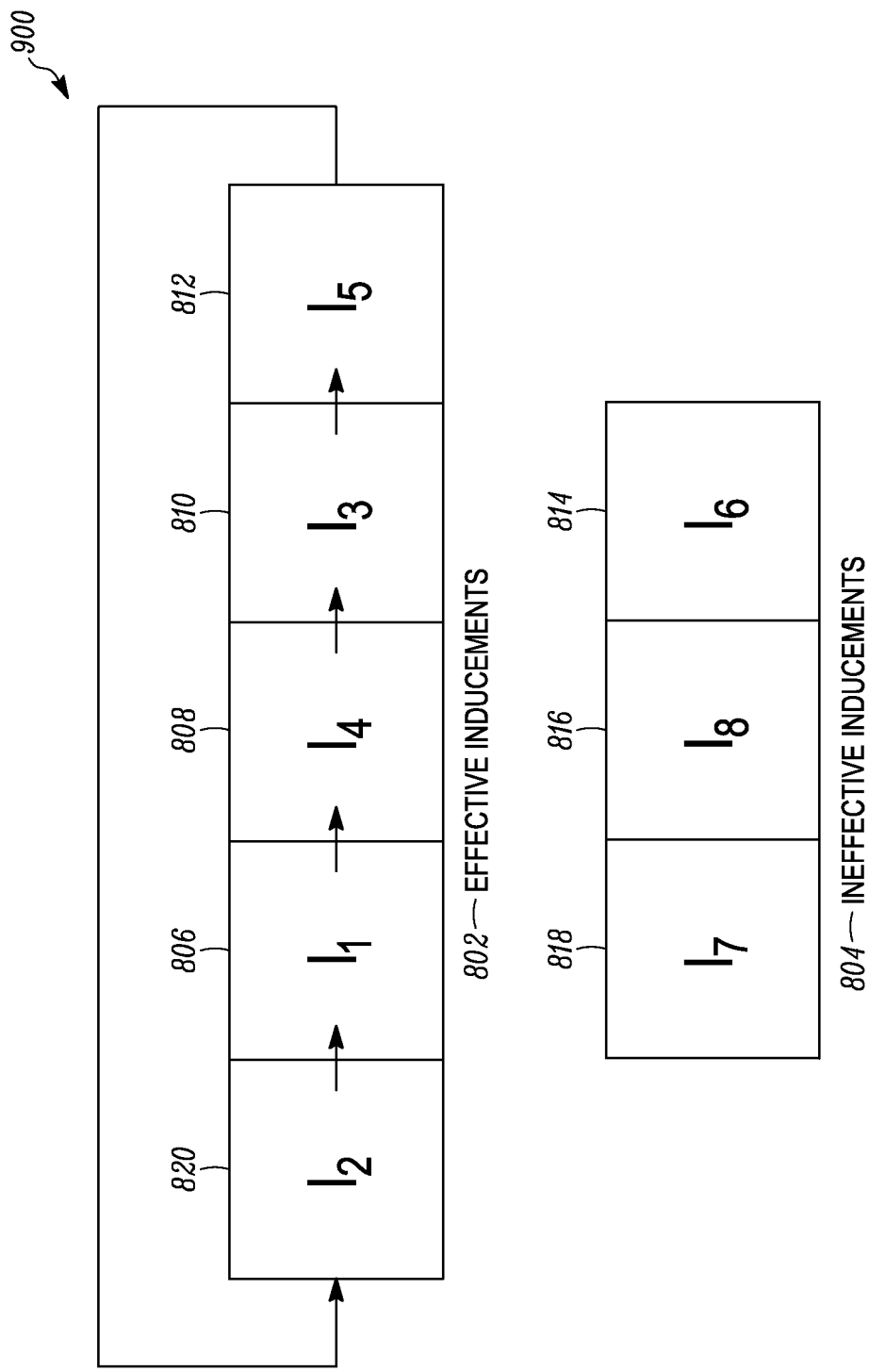
FIG. 9 is a schematic diagram illustrating a method for selecting a blink inducement in accordance with an embodiment.

In other embodiments, the device 102 selects the first blink inducement to present again before selecting the second blink inducement to present again when the effectiveness score for the first blink inducement is greater than the effectiveness score for the second blink inducement. FIGS. 8 and 9 illustrate one such embodiment. Specifically, FIG. 8 shows a schematic diagram 800 illustrating a method for selecting a blink inducement to present to a user. The plurality of eight blink inducements of table 602 populate two sets of blink inducements, a set 802 of effective blink inducements and a set 804 of ineffective blink inducements. The set 802 of effective blink inducements includes, from left to right, the blink inducements $I_1$ 806, $I_4$ 808, $I_3$ 810, $I_5$ 812, and $I_6$ 814, each of which has an effectiveness score listed in table 602 of above 0.5. Effective blink inducements for the present embodiment are those blink inducements with effectiveness scores above 0.5. From right to left, the blink inducements $I_8$ 816, $I_7$ 818, and $I_2$ 820 are included in the set 804 of ineffective blink inducements. Ineffective blink inducements for the present embodiment are those blink inducements with effectiveness scores of 0.5 or lower, which are at best able to induce a user to blink only half the time.

The device 102 selects the blink inducement $I_6$ 814 from the right end of the set 802 of effective blink inducements. Upon presenting the blink inducement $I_6$ 814, the device 102 determines the user did not blink. The device 102 then updates the effectiveness score for the blink inducement $I_6$ 814 from 0.75 to 0.5. Based on the updated effectiveness score of 0.5, the blink inducement $I_6$ 814 now identifies as an ineffective blink inducement. Therefore, after being stripped away from the right end of the set 802 of effective blink inducements, the blink inducement $I_6$ 814 is added to the right end of the set 804 of ineffective blink inducements. The ineffective blink inducement $I_2$ 820 is displaced from the left end of the set 804 of ineffective blink inducements and added to the left end of the set 802 of effective blink inducements. This is based on reasoning, for instance, that because the blink inducement $I_2$ 820 has not been selected in a while, it might again be effective at inducing the user to blink.

FIG. 9 shows a schematic diagram 900 illustrating the next selection of a blink inducement. The diagram 900 shows the two sets 802, 804 of blink inducements of the diagram 800 after the selection of the blink inducement $I_6$ 814. The blink inducement $I_6$ 814 now appears at the right end of the set 804 of ineffective blink inducements, and the blink inducement $I_2$ 820 now appears at the left end of the set 802 of effective blink inducements. When the device 102 next selects a blink inducement, it selects the blink inducement $I_5$ 812 from the right end of the set 802 of effective blink inducements and presents it to the user.

The device 102 determines that the user blinked in response to being presented the blink inducement $I_5$ 812 and proceeds to update the effectiveness score for the blink inducement $I_5$ 812. In this instance, the effectiveness score for the blink inducement $I_5$ 812 either remains at a value of 0.75 if the last time the user failed to blink remains within the last four presentations of the blink inducement $I_5$ 812, or it changes to a value of 1.0 if the last time the user failed to blink is no longer within the last four presentations of the blink inducement $I_5$ 812. In each case, the updated effectiveness score for the blink inducement $I_5$ 812 remains above 0.5. The device 102 keeps the blink inducement $I_5$ 812 in the set 802 of effective blink inducements by stripping it from the right side of the set 802 and adding it to the left side of the same set 802. The next blink inducement the device 102 selects is $I_3$ 810. Because an effectiveness score of 0.75 or 1.0 for the blink inducement $I_5$ 812 is greater than the effectiveness score of 0.5 for the blink inducement $I_6$ 814, the blink inducement $I_5$ 812 will cycle through the set 802 of effective blink inducements and be selected again before the blink inducement $I_6$ 814 can cycle through both the set 804 of ineffective blink inducements and the set 802 of effective blink inducements.

For one embodiment, as the ratio of the number of blink inducements with effectiveness scores above a threshold effectiveness score to the number of blink inducements with effectiveness scores at or below the threshold effectiveness score changes, the relative number of blink inducements in the two sets 802, 804 of blink inducements changes. In an alternate embodiment, a fixed number of n ineffective blink inducements are identified from a plurality of blink inducements simply as those blink inducements in the plurality of blink inducements with the lowest effectiveness scores.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not explicitly listed or inherent to such process, method, article, or apparatus. An element proceeded by "comprises a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A method performed by an electronic computing device for managing blinking, the method comprising:
    detecting blinking of a user of the electronic computing device;
    determining, from the detected blinking, an uninduced blink rate for the user; and
    inducing the user to blink based on the uninduced blink rate.

2. The method of claim 1, wherein inducing the user to blink based on the uninduced blink rate comprises:
    comparing the uninduced blink rate to a threshold blink rate; and inducing the user to blink when the uninduced blink rate is below the threshold blink rate.

3. The method of claim 2, wherein inducing the user to blink comprises presenting the user with a set of blink inducements.

4. The method of claim 3, wherein blink inducements of the set of blink inducements are presented to the user at a presented inducement rate.

5. The method of claim 4, wherein the presented inducement rate is greater than or equal to a difference between the threshold blink rate and the uninduced blink rate.

6. The method of claim 4 further comprising determining an induced blink rate from the presented inducement rate, wherein the presented inducement rate is adjusted based on the induced blink rate so that the induced blink rate is greater than or equal to a difference between the threshold blink rate and the uninduced blink rate.

7. The method of claim 1, wherein inducing the user to blink comprises presenting the user with a first presentation of a first blink inducement of a plurality of blink inducements, the method further comprising:
  determining whether the user blinked in response to the first presentation of the first blink inducement; and
  presenting the user with a second presentation of the first blink inducement based on the determination of whether the user blinked in response to the first presentation of the first blink inducement.

8. The method of claim 7 further comprising determining an effectiveness score for the first blink inducement based on the determination of whether the user blinked in response to the first presentation of the first blink inducement, wherein presenting the user with the second presentation of the first blink inducement is based on the effectiveness score.

9. A method performed by an electronic computing device for managing blinking, the method comprising:
  presenting a user of the electronic computing device with a first blink inducement of a plurality of blink inducements;
  determining whether the user blinked in response to presenting the first blink inducement;
  presenting the first blink inducement again based on the determination of whether the user blinked in response to presenting the first blink inducement.

10. The method of claim 9 further comprising determining, based on whether the user blinked in response to presenting the first blink inducement, a first effectiveness score for the first blink inducement, wherein presenting the first blink inducement to the user again is based on the first effectiveness score.

11. The method of claim 10, wherein determining the first effectiveness score comprises determining whether the user blinked in response to the first blink inducement each time of multiple times the first blink inducement was presented.

12. The method of claim 10 further comprising:
  presenting the user of the electronic computing device with a second blink inducement of the plurality of blink inducements;
  determining if the user blinked in response to presenting the second blink inducement;
  determining, based on whether the user blinked in response to presenting the second blink inducement, a second effectiveness score for the second blink inducement; and
  determining whether the first effectiveness score is greater than the second effectiveness score.

13. The method of claim 12 further comprising selecting the first blink inducement to present again before selecting the second blink inducement to present again when the first effectiveness score is greater than the second effectiveness score.

14. The method of claim 12 further comprising selecting the first blink inducement to present again with a greater statistical likelihood than selecting the second blink inducement to present again when the first effectiveness score is greater than the second effectiveness score.

15. The method of claim 9 further comprising:
  monitoring an uninduced blink rate for the user; and
  presenting at least one blink inducement from the plurality of blink inducements at a presented inducement rate, wherein the presented inducement rate is based on a difference between a threshold blink rate and the uninduced blink rate.

16. The method of claim 15, wherein at least one of:
  the presented inducement rate has an inverse relationship with the uninduced blink rate; or
  the presented inducement rate is zero when the uninduced blink rate is greater than the threshold blink rate.

17. An electronic computing device configured to manage blinking, the electronic computing device comprising:
  at least one blink sensor module configured to receive blink sensor data;
  at least one blink inducement module configured to present a plurality of blink inducements; and
  a processing element operatively coupled to the at least one blink sensor module and the at least one blink inducement module, wherein the processing element is configured to:
    present, using the blink inducement module, a blink inducement from the plurality of blink inducements;
    determine, based on the blink sensor data received by the at least one blink sensor module, whether a user of the electronic computing device blinked in response to the presented blink inducement; and
    present the blink inducement again based on the determination of whether the user blinked in response to the presented blink inducement.

18. The electronic computing device of claim 17, wherein at least one of:
  the at least one blink sensor module comprises a camera; or
  the at least one blink inducement module comprises a display screen.

19. The electronic computing device of claim 17, wherein the processing element is further configured to:
  determine, based on the blink sensor data received by the at least one blink sensor module, an uninduced blink rate for the user; and
  present, using the blink inducement module, the user with additional blink inducements from the plurality of blink inducements at a presented inducement rate based on the determined uninduced blink rate.

20. The electronic computing device of claim 19, wherein the processing element is further configured to:
  monitor, using the at least one blink sensor module, a combined blink rate for the user; and
  adjust the presented inducement rate based on the monitored combined blink rate so that at least one of:
    the presented inducement rate increases as the monitored combined blink rate decreases; or
    the presented inducement rate decreases as the monitored combined blink rate increases.

* * * * *